United States Patent
Huang

(10) Patent No.: US 11,679,301 B2
(45) Date of Patent: Jun. 20, 2023

(54) STEP COUNTING METHOD AND APPARATUS FOR TREADMILL

(71) Applicant: Huawei Technologies Co., Ltd., Shenzhen (CN)

(72) Inventor: Xiaoping Huang, Shanghai (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 963 days.

(21) Appl. No.: 16/479,426

(22) PCT Filed: May 27, 2017

(86) PCT No.: PCT/CN2017/086274
§ 371 (c)(1),
(2) Date: Jul. 19, 2019

(87) PCT Pub. No.: WO2018/133279
PCT Pub. Date: Jul. 26, 2018

(65) Prior Publication Data
US 2019/0381356 A1     Dec. 19, 2019

(30) Foreign Application Priority Data
Jan. 19, 2017   (CN) .......................... 201710039884.5

(51) Int. Cl.
A63B 24/00     (2006.01)
A61B 5/11      (2006.01)
(Continued)

(52) U.S. Cl.
CPC .......... *A63B 24/0062* (2013.01); *A61B 5/112* (2013.01); *A61B 5/7203* (2013.01);
(Continued)

(58) Field of Classification Search
CPC ................ A63B 24/0062; A63B 22/02; A63B 2071/0675; A63B 2220/40;
(Continued)

(56) References Cited

U.S. PATENT DOCUMENTS 9,390,229 B1    7/2016  Kahn et al.
2005/0272564 A1* 12/2005 Pyles ................. A63B 22/0257
                                                        482/8
(Continued)

FOREIGN PATENT DOCUMENTS

CN           1861227 A      11/2006
CN         101116769 A       2/2008
(Continued)

OTHER PUBLICATIONS

Orr K., et al., "Validity of smartphone pedometer applications," BMC Research Notes (2015), Nov. 30, 2015, vol. 8, No. 1, 9 pages.
(Continued)

*Primary Examiner* — Marisol Figueroa
(74) *Attorney, Agent, or Firm* — Conley Rose, P.C.

(57) ABSTRACT

A step counting apparatus for a treadmill includes a terminal device. The terminal device is placed on the treadmill. The terminal device includes an acceleration sensor, a processor and a memory. The memory is configured to store a software program. The acceleration sensor is configured to collect a vibration signal generated when a user runs on the treadmill. The processor is configured to execute the software program stored in the memory, to cause the processor to instruct the acceleration sensor to collect the vibration signal generated when the user runs on the treadmill. The processor is further configure to execute the software program to analyze, using a time-frequency analysis algorithm, the vibration signal to determine a quantity of exercise steps of the user on the treadmill.

20 Claims, 6 Drawing Sheets

---

S201

A terminal device collects, by using an acceleration sensor, a vibration signal generated when a user runs on a treadmill

S202

The terminal device analyzes, by using a time-frequency analysis algorithm, the vibration signal to determine a quantity of sports steps of the user on the treadmill

(51) Int. Cl.
*A63B 22/02* (2006.01)
*G01C 22/00* (2006.01)
*A63B 71/06* (2006.01)
*A61B 5/00* (2006.01)

(52) U.S. Cl.
CPC ............ *A61B 5/7257* (2013.01); *A63B 22/02* (2013.01); *G01C 22/00* (2013.01); *G01C 22/006* (2013.01); *A63B 2071/0675* (2013.01); *A63B 2220/40* (2013.01)

(58) Field of Classification Search
CPC ............ A63B 2220/17; A63B 71/0622; A63B 2220/64; A63B 2220/833; A63B 2220/20; A63B 2220/22; A63B 2220/62; A61B 5/112; A61B 5/7203; A61B 5/7257; G01C 22/00; G01C 22/006; H04M 1/72454; G01P 15/097
See application file for complete search history.

(56) References Cited

U.S. PATENT DOCUMENTS

| | | | |
|---|---|---|---|
| 2008/0242512 | A1 | 10/2008 | Kim et al. |
| 2009/0299691 | A1* | 12/2009 | Shimaoka ............ G01C 22/006 702/160 |
| 2012/0209532 | A1* | 8/2012 | Liang .................... G16H 20/30 702/19 |
| 2013/0231889 | A1* | 9/2013 | Hrybyk ................. G01C 22/006 702/141 |
| 2014/0129177 | A1 | 5/2014 | Gyorfi et al. |
| 2014/0221160 | A1* | 8/2014 | Hardy ................. A63B 24/0062 482/8 |
| 2015/0262470 | A1 | 9/2015 | Munro et al. |

FOREIGN PATENT DOCUMENTS

| | | |
|---|---|---|
| CN | 201132032 Y | 10/2008 |
| CN | 201430692 Y | 3/2010 |
| CN | 104937376 A | 9/2015 |
| CN | 106092130 A | 11/2016 |
| CN | 106166365 A | 11/2016 |
| CN | 106310588 A | 1/2017 |
| DE | 202012013329 U1 | 5/2016 |
| EP | 2894481 A1 | 7/2015 |
| KR | 20000059241 A | 10/2000 |
| KR | 20110030923 A | 3/2011 |
| KR | 101661700 B1 | 10/2016 |

OTHER PUBLICATIONS

Machine Translation and Abstract of Chinese Publication No. CN106310588, Jan. 11, 2017, 15 pages.
Orr, K., et al., "Validity of smartphone pedometer applications," XP055644395, BMC Research Notes, Nov. 30, 2015, 9 pages.
Foreign Communication From A Counterpart Application, European Application No. 17893429.5, Extended European Search Report dated Nov. 29, 2019, 8 pages.
Foreign Communication From A Counterpart Application, Chinese Application No. 201780009091.7, Chinese Office Action dated Dec. 23, 2019, 11 pages.
Machine Translation and Abstract of Chinese Publication No. CN1861227, Nov. 15, 2006, 15 pages.
Machine Translation and Abstract of Chinese Publication No. CN101116769, Feb. 6, 2008, 9 pages.
Machine Translation and Abstract of Chinese Publication No. CN106092130, Nov. 9, 2016, 16 pages.
Machine Translation and Abstract of Chinese Publication No. CN106166365, Nov. 30, 2016, 20 pages.
Machine Translation and Abstract of Chinese Publication No. CN201132032, Oct. 15, 2008, 14 pages.
Machine Translation and Abstract of Chinese Publication No. CN201430692, Mar. 24, 2010, 7 pages.
Machine Translation and Abstract of German Publication No. DE202012013329, May 20, 2016, 15 pages.
Foreign Communication From A Counterpart Application, Chinese Application No. 201780009091.7, Chinese Office Action dated Jun. 24, 2019, 5 pages.
Foreign Communication From A Counterpart Application, PCT Application No. PCT/CN2017/086274, English Translation of International Search Report dated Nov. 9, 2017, 2 pages.
Foreign Communication From A Counterpart Application, PCT Application No. PCT/CN2017/086274, English Translation of Written Opinion dated Nov. 9, 2017, 3 pages.

* cited by examiner

… (1) …

STEP COUNTING METHOD AND APPARATUS FOR TREADMILL

CROSS-REFERENCE TO RELATED APPLICATIONS

This application is a national stage application of International Application No. PCT/CN2017/086274, filed on May 27, 2017, which claims priority to Chinese Patent Application No. 201710039884.5, filed on Jan. 19, 2017. Both of the aforementioned applications are hereby incorporated by reference in their entireties.

This application claims priority to Chinese Patent Application No. 201710039884.5, filed with the Chinese Patent Office on Jan. 19, 2017 and entitled "METHOD AND DEVICE FOR IMPLEMENTING STEP COUNTING FOR TREADMILL BY USING ACCELERATION SENSOR OF MOBILE PHONE", which is incorporated herein by reference in its entirety.

TECHNICAL FIELD

This application relates to the field of signal processing technologies, and in particular, to a step counting method and apparatus for a treadmill.

BACKGROUND

With improvement of people's living standards, people are paying more attention to their health. Learning of quantities of steps people have walked or run every day can help them learn an exercise case in real time, thereby helping them make a proper health plan. Currently, people usually learn of quantities of exercise steps in real time by using a pedometer or a mobile phone.

However, when running on a treadmill, people need to wear an additional sports accessory to count steps, for example, a smartwatch, a bracelet, or a smart step counting headset. In comparison, costs are higher. In addition, steps are alternatively counted by using a smart treadmill. Then the smart treadmill and a mobile phone establish a connection through Bluetooth, infrared, or another short range communication means, so that people obtain quantities of exercise steps from the mobile phone. However, smart treadmills are not widely used currently, and actual experience obtained by users is relatively little.

SUMMARY

Embodiments of this application provide a step counting method and apparatus for a treadmill, to resolve a problem of high costs in the prior art.

According to a first aspect, an embodiment of this application provides a step counting method for a treadmill. The method is applied to a terminal device, and the terminal device is placed on the treadmill. The method includes: collecting, by the terminal device by using an acceleration sensor a vibration signal generated when a user runs on the treadmill; and analyzing, by the terminal device by using a time-frequency analysis algorithm, the vibration signal to determine a quantity of exercise steps of the user on the treadmill.

in the foregoing design, the acceleration sensor of the terminal device is used to collect the vibration signal of the treadmill when the user runs, and the quantity of steps of the user is identified through the time-frequency analysis algorithm. Quantities of exercise steps of the user are converged to improve social ranking performance, thereby enhancing user experience. In addition, no additional step counting device for running is needed any more, which reduces costs of the user.

The time-frequency analysis algorithm may be an algorithm such as Fourier transform, wavelet transform, or Wigner-Ville distribution, or analysis of a combination of the foregoing two or more. This is not specifically limited in this embodiment of this application.

In a possible design, before the analyzing, by the terminal device by using a time-frequency analysis algorithm, the vibration signal to determine a quantity of exercise steps of the user on the treadmill, the method further includes: denoising, by the terminal device, the vibration signal.

In the foregoing design, the vibration signal is inevitably mingled with noise. Therefore, denoising the vibration signal improves accuracy of step counting for the treadmill to some extent.

In a possible design, the denoising, by the terminal device, the vibration signal includes: identifying, by the terminal device, a vibration component of the treadmill in the vibration signal based on a vibration frequency of the treadmill; and filtering out the vibration component of the treadmill in the vibration signal, where the vibration frequency of the treadmill is a vibration frequency obtained after the treadmill is started and when no user runs on the treadmill.

Because the vibration component of the treadmill is very regular, a spectral component of the vibration component of the treadmill is identified, and then a corresponding spectral component in the signal collected when the user runs is filtered out, so that a relatively clean vibration signal when the user runs can be obtained, facilitating next step counting processing. Specifically, the vibration component of the treadmill in the vibration signal may be filtered out by using a finite impulse response (Finite Impulse Response, FIR for short) filter, an infinite impulse response (Infinite impulse Response, IIR for short) filter, or the like.

In a possible design, the analyzing, by the terminal device by using a time-frequency analysis algorithm, the vibration signal to determine a quantity of exercise steps of the user on the treadmill includes: performing, by the terminal device, fast Fourier filtering processing on the vibration signal to obtain a filtered signal; and determining, by the terminal device, a quantity of crests whose peaks are greater than a preset threshold in the filtered signal as the quantity of exercise steps of the user.

Through the foregoing design, a simple and effective manner of determining the quantity of exercise steps based on the vibration signal is provided.

in a possible design, before the collecting, by the terminal device by using an acceleration sensor, a vibration signal generated when a user runs on the treadmill, the method further includes: identifying, by the terminal device, that the terminal device is in treadmill mode, where the treadmill mode indicates that the terminal device is placed on the treadmill.

Through the foregoing design, a general running mode and a treadmill mode are distinguished. For the treadmill mode, the step counting manner provided in this embodiment of this application is used, while for the general running mode, a step counting manner provided in the prior art may be used.

In a possible design, after the analyzing, by the terminal device by using a time-frequency analysis algorithm, the vibration signal to determine a quantity of exercise steps of the user on the treadmill, the method further includes: updating, by the terminal device, the quantity of exercise steps of the user that is recorded in the terminal device, and notifying the user of an updated quantity of exercise steps of the user.

Through the foregoing design, the user can learn of the quantity of exercise steps on the treadmill by using only the terminal device, without needing an additional device such a sports bracelet or a sports headset, which reduces costs of the user and provides convenience for the user.

In a possible design, the method further includes: recording, by the terminal device, duration of the vibration signal generated when the user runs on the treadmill; and after the analyzing, by the terminal device by using a time-frequency analysis algorithm, the vibration signal to determine a quantity of exercise steps of the user on the treadmill, determining, by the terminal device based on the quantity of exercise steps of the user on the treadmill and the duration, a stride frequency of the user during running on the treadmill, and notifying the user of the stride frequency of the user.

Through the foregoing design, the user can learn, by using the terminal device, of both the quantity of exercise steps on the treadmill and the stride frequency during running, without needing an additional device such a sports bracelet or a sports headset, which reduces costs of the user and provides convenience for the user.

In a possible design, after the analyzing, by the terminal device by using a time-frequency analysis algorithm, the vibration signal to determine a quantity of exercise steps of the user on the treadmill, the method further includes: estimating, by the terminal device, an exercise distance of the user on the treadmill based on a stride length of the user and the quantity of exercise steps of the user on the treadmill, and notifying the user of the exercise distance of the user on the treadmill, where the stride length is obtained by the terminal device by collecting statistics based on a non-treadmill running case of the user in a past period of time.

Through the foregoing design, the user can learn, by using the terminal device, of both the quantity of exercise steps on the treadmill and the distance of running on the treadmill. Exercise distances are converged to improve social ranking performance. In addition, no additional device such a sports bracelet or a sports headset is needed, which reduces costs of the user and provides convenience for the user.

According to a second aspect, an embodiment of this application provides a step counting apparatus for a treadmill. The apparatus is applied to a terminal device, and the terminal device is placed on the treadmill. The apparatus includes an acceleration sensor, a processor, and a. memory.

The memory is configured to store a software program.

The acceleration sensor is configured to collect a vibration signal generated when a user runs on the treadmill.

The processor is configured to execute the software program stored in the memory, and is specifically configured to instruct the acceleration sensor to: collect the vibration signal generated when the user runs on the treadmill, and analyze, by using a time-frequency analysis algorithm, the vibration signal to determine a quantity of exercise steps of the user on the treadmill.

In a possible design, the processor is further configured to denoise the vibration signal before analyzing, by using the time-frequency analysis algorithm, the vibration signal to determine the quantity of exercise steps of the user on the treadmill.

In a possible design, when denoising the vibration signal, the processor is specifically configured to:

identify a vibration component of the treadmill in the vibration signal based on a. vibration frequency of the treadmill; and filter out the vibration component of the treadmill in the vibration signal, where the vibration frequency of the treadmill is a vibration frequency obtained after the treadmill is started and when no user runs on the treadmill.

In a possible design, when analyzing, by using the time-frequency analysis algorithm, the vibration signal to determine the quantity of exercise steps of the user on the treadmill, the processor is specifically configured to:

perform fast Fourier filtering processing on the vibration signal to obtain a filtered signal; and determine a quantity of crests whose peaks are greater than a preset threshold in the filtered signal as the quantity of exercise steps of the user.

In a possible design, the processor is further configured to identify, before the vibration signal generated when the user runs on the treadmill is collected by using the acceleration sensor, that the terminal device is in treadmill mode, where the treadmill mode indicates that the terminal device is placed on the treadmill.

In a possible design, the processor is further configured to:

update, after analyzing, by using the time-frequency analysis algorithm, the vibration signal to determine the quantity of exercise steps of the user on the treadmill, the quantity of exercise steps of the user that is recorded in the memory, and notify the user of an updated quantity of exercise steps of the user.

In a possible design, the processor is further configured to: record, in the memory, duration of the vibration signal generated when the user runs on the treadmill; and after analyzing, by using the time-frequency analysis algorithm, the vibration signal to determine the quantity of exercise steps of the user on the treadmill, determine, based on the quantity of exercise steps of the user on the treadmill and the duration, a stride frequency of the user during running on the treadmill, and notify the user of the stride frequency of the user.

In a possible design, the processor is further configured to: after analyzing, by using the time-frequency analysis algorithm, the vibration signal to determine the quantity of exercise steps of the user on the treadmill, estimate an exercise distance of the user on the treadmill based on a. stride length of the user and the quantity of exercise steps of the user on the treadmill, and notify the user of the exercise distance of the user on the treadmill, where the stride length is obtained by the terminal device by collecting statistics based on a non-treadmill running case of the user in a past period of time.

According to a third aspect, an embodiment of this application provides a step counting apparatus for a treadmill. The apparatus is applied to a terminal device, and the terminal device is placed on the treadmill. The apparatus includes:

a collection module, configured to collect, by using an acceleration sensor, a vibration signal generated when a user runs on the treadmill; and a processing module, configured to analyze, by using a time-frequency analysis algorithm, the vibration signal to determine a quantity of exercise steps of the user on the treadmill.

In a possible design, the apparatus further includes:

a denoising module, configured to denoise the vibration signal before the processing module analyzes, by using the time-frequency analysis algorithm, the vibration signal to determine the quantity of exercise steps of the user on the treadmill.

In a possible design, the denoising module is specifically configured to: identify a vibration component of the treadmill in the vibration signal based on a vibration frequency of the treadmill; and filter out the vibration component of the treadmill in the vibration signal, where the vibration frequency of the treadmill is a vibration frequency obtained after the treadmill is started and when no user runs on the treadmill.

In a possible design, the apparatus further includes:

a filtering module, configured to perform fast Fourier filtering processing on the vibration signal to obtain a filtered signal.

The processing module is specifically configured to determine a quantity of crests whose peaks are greater than a preset threshold in the filtered signal as the quantity of exercise steps of the user.

In a possible design, the apparatus further includes:

an identification module, configured to identify, before the collection module collects, by using the acceleration sensor, the vibration signal generated when the user runs on the treadmill, that the terminal device is in treadmill mode, where the treadmill mode indicates that the terminal device is placed on the treadmill.

In a possible design, the apparatus further includes:

a recording module, configured to update, after the processing module analyzes, by using the time-frequency analysis algorithm, the vibration signal to determine the quantity of exercise steps of the user on the treadmill, the quantity of exercise steps of the user that is recorded in the terminal device; and a notification module, configured to notify the user of an updated quantity of exercise steps of the user.

In a possible design, the recording module is configured to record duration of the vibration signal generated when the user runs on the treadmill;

after analyzing, by using the time-frequency analysis algorithm, the vibration signal to determine the quantity of exercise steps of the user on the treadmill, the processing module determines, based on the quantity of exercise steps of the user on the treadmill and the duration, a stride frequency of the user during running on the treadmill; and the notification module is configured to notify the user of the stride frequency of the user.

In a possible design, the processing module is configured to: after analyzing, by using the time-frequency analysis algorithm, the vibration signal to determine the quantity of exercise steps of the user on the treadmill, estimate an exercise distance of the user on the treadmill based on a stride length of the user and the quantity of exercise steps of the user on the treadmill, where the stride length is obtained by the terminal device by collecting statistics based on a non-treadmill running case of the user in a past period of time; and the notification module is configured to notify the user of the exercise distance of the user on the treadmill, According to a fourth aspect, an embodiment of this application provides a computer-readable storage medium. The computer-readable storage medium stores a software program. When being read and executed by one or more processors, the software program is capable of implementing the foregoing method.

According to a fifth aspect, an embodiment of this application provides a computer program product including an instruction. When the computer program product is run on a computer, the computer is enabled to perform the foregoing method.

DESCRIPTION OF EMBODIMENTS

When running on a treadmill, a user is usually accustomed to placing a mobile phone or the like on the treadmill, for example, on a storage tank of the treadmill. Based on the foregoing found regularity, embodiments of this application provide a step counting method and apparatus for a treadmill. An acceleration sensor of a terminal device is used to collect a vibration signal of the treadmill when a user runs, and a quantity of steps of the user is identified by using a. time-frequency analysis algorithm. Quantities of exercise steps of the user are converged to improve social ranking performance, thereby enhancing user experience. In addition, no additional step counting device for running is needed any more, which reduces costs of the user.

The method and the apparatus are based on a same inventive concept. Because principles of the method and the apparatus for resolving a problem are similar, for implementations of the apparatus and the method, refer to each other, and repeated descriptions are omitted.

Some wordings in this application are explained below for ease of understanding by a person skilled in the art.

A stride frequency refers to a quantity of steps of a user per unit time, for example, 3.5 steps/second.

A stride length refers to a distance of a step the user walks or run, for example, 70 cm/step.

"A plurality of" refers to at least two.

The step counting solutions for the treadmill in the embodiments of this application may be implemented by using a terminal device. The terminal device includes, but is not limited to, a personal computer, a server computer, a handheld or laptop device, a mobile device (for example, a mobile phone, a mobile telephone, a tablet computer, a personal digital assistant, or a media player), an electronic device of a consumption type, a small computer, a mainframe computer, or the like. The solutions provided in the embodiments of this application are specifically described below by using a mobile phone as an example.

Figure 1:
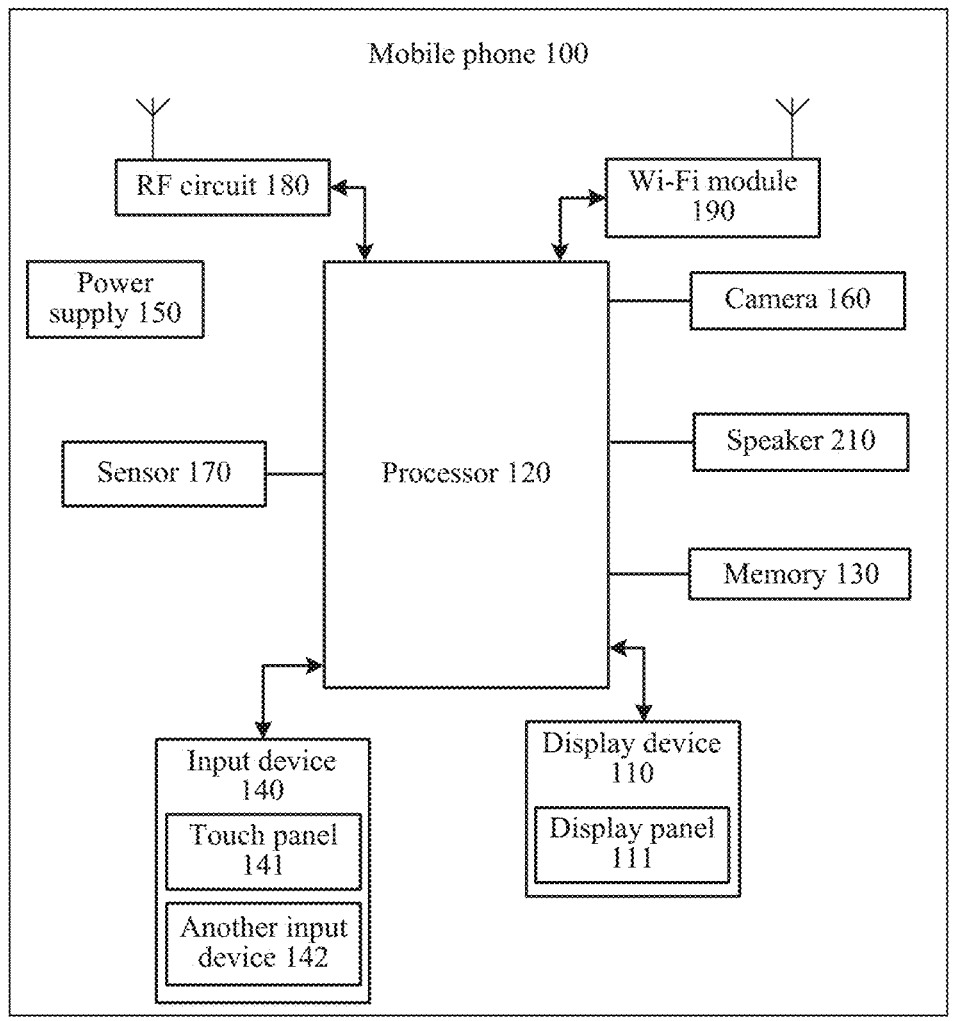
FIG. 1 is a schematic structural diagram of a mobile phone according to an embodiment of this application.

FIG. 1 is a schematic structural diagram of hardware of a mobile phone to which an embodiment of this application is applied. As shown in FIG. 1, the mobile phone 100 includes a display device 110, a processor 120, and a memory 130. The memory 130 may be configured to store a software program and data. The processor 120 runs the software program and the data stored in the memory 130, to implement various functional applications of the mobile phone 100 and process data. The memory 130 may mainly include a program storage area and a data storage area. The program storage area may store an operating system, an application program required by at least one function (for example, an image capturing function), or the like. The data storage area may store data (for example, audio data, an address book, and an exchangeable image file EXIT) created according to use of the mobile phone 100, or the like. In addition, the memory 120 may include a high-speed random access memory, and may further include a non-volatile memory, such as at least one magnetic disk storage device, a flash memory device, or another volatile solid-state storage device. The processor 120 is a control center of the mobile phone 100, and is connected to various parts of the entire mobile phone by using various interfaces and lines. By running or executing the software program and/or the data stored in the memory 130, the processor 120 performs various functions of the mobile phone 100 and processes data, thereby performing overall monitoring on the mobile phone. The processor 120 may include one or more general-purpose processors, may further include one or more DSPs (Digital Signal Processor, digital signal processor), and is configured to perform related operations, to implement the technical solutions provided in the embodiments of this application.

The mobile phone 100 further includes a camera 160 configured to take photos or shoot videos. The mobile phone 100 may further include an input device 140, configured to: receive input digit information and character information, or a contact-type touch operation/a non-contact-type gesture, and generate a signal input related to user setting and function control of the mobile phone 100, or the like. Specifically, in this embodiment of this application, the input device 140 may include a touch panel 141. The touch panel 141, also referred to as a touchscreen, may collect a. touch operation performed by a user on or near the touch panel 141 (for example, an operation performed by the user on the touch panel 141 or near the touch panel 141 by using any suitable object or accessory such as a finger or a stylus), and drive a corresponding connection apparatus based on a preset program. Optionally, the touch panel 141 may include two parts: a touch detection apparatus and a touch controller. The touch detection apparatus detects a touch position of the user, detects a signal generated by the touch operation, and transfers the signal to the touch controller The touch controller receives touch information from the touch detection apparatus, converts the touch information into touch point coordinates, and then sends the touch point coordinates to the processor 120. Moreover, the touch controller can receive and execute a command sent from the processor 120. For example, the user clicks, by using a finger, on an icon, a legend, or the like for starting step counting of the treadmill on the touch panel 141. The touch detection apparatus detects a signal resulting from the click, and then transfers the signal to the touch controller. The touch controller then converts the signal into coordinates, and then sends the coordinates to the processor 120. The processor 120 determines an operation (starting) on the icon or the legend based on the coordinates and a type of the signal (click or double-click), then determines memory space needing to be occupied for performing the operation, and if the memory space needing to be occupied is less than free memory, starts the treadmill to count steps.

The touch panel 141 may be a resistive, capacitive, infrared, surface sound wave type touch panel, or the like. Besides the touch panel 141, the input unit 140 may further include another input device 142. The another input device 142 may include, but is not limited to, one or more of a physical keyboard, a function key (for example, a volume control key or a switch key), a track ball, a mouse, a joystick, or the like.

A display panel 111 included in the display device 110 is configured to display information entered by the user, information provided to the user, various menu interfaces of the mobile phone 100, or the like, and in this embodiment of this application, is mainly configured to display an image captured by a camera of the mobile phone 100. Optionally, the display panel 111 may be configured in a form of a liquid crystal display (English: Liquid Crystal Display, LCD for short), an organic light-emitting diode (English: Organic Light-Emitting Diode, OLED for short), or the like. In some other embodiments, the touch panel 141 may cover the display panel 111, to form a touch display screen.

Besides, the mobile phone 100 may further include a power supply 150 configured to supply power to other modules. The mobile phone 100 may further include one or more sensors 170, for example, an acceleration sensor, a light sensor, a GPS sensor, an infrared sensor, a laser sensor, a location sensor, or a lens pointing angle sensor. The mobile phone 100 may further include a radio frequency (Radio Frequency, RF) circuit 180, configured to perform network communication with a wireless network device, may further include a Wi-Fi module 190, configured to perform Wi-Fi communication with another device, and may further include a speaker 210, configured to play music, prompt through voice, make a prompt tone, or the like.

Figure 2:
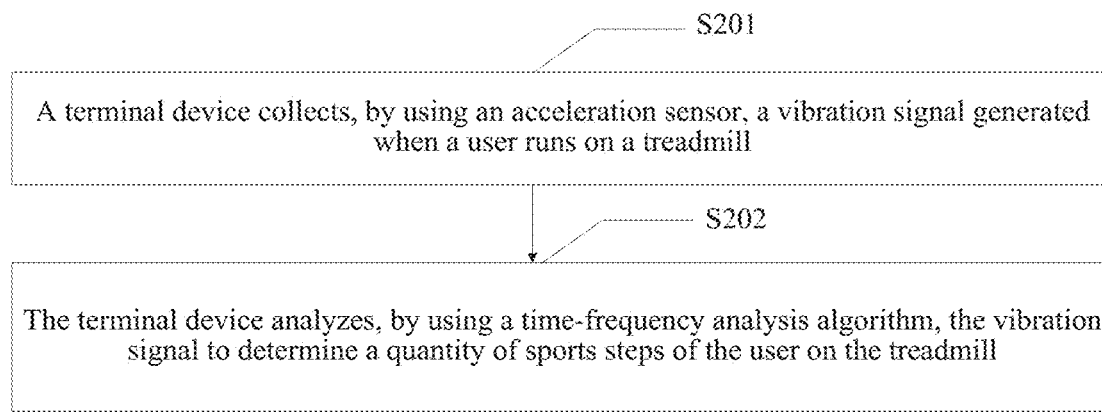
FIG. 2 is a flowchart of a step counting method for a treadmill according to an embodiment of this application.

A step counting method for a treadmill provided in an embodiment of this application may be implemented in the stored software program shown in FIG. 1, may be specifically performed by the processor 120. Referring to FIG. 2, the method specifically includes:

S201: A terminal device collects, by using an acceleration sensor, a vibration signal generated when a user runs on the treadmill.

S202: The terminal device analyzes, by using a time-frequency analysis algorithm, the vibration signal to determine a quantity of exercise steps of the user on the treadmill.

The time-frequency analysis algorithm may be an algorithm such as Fourier transform, wavelet transform, or Wigner-Ville distribution, or analysis of a combination of the foregoing two or more. This is not specifically limited in the embodiments of this application.

For example, that the terminal device analyzes, by using a time-frequency analysis algorithm, the vibration signal to determine a quantity of exercise steps of the user on the treadmill is implemented in the following manner:

performing, by the terminal device, fast Fourier filtering processing on the vibration signal to obtain a filtered signal; and determining, by the terminal device, a quantity of crests whose peaks are greater than a preset threshold in the filtered signal as the quantity of exercise steps of the user.

Figure 3A:
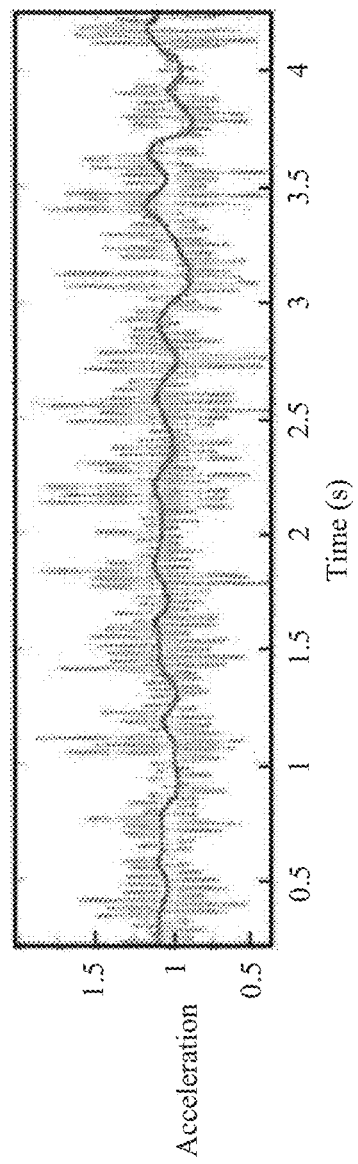
FIG. 3A and FIG. 3B are schematic diagrams of generating a vibration signal when a user runs on a treadmill according to an embodiment of this application.

FIG. 3A is a time domain diagram of the vibration signal collected by the acceleration sensor when the user runs on the treadmill. In this way, it may be learned from FIG. 3A that a signal whose acceleration is approximately 30 Hz has a relatively high energy proportion. In addition, it may be learned from FIG. 3A that there is an obvious envelope signal of 2 Hz, and the envelope signal corresponds to a stride frequency during running, to be specific, the stride frequency during running at this moment is 120, thereby implementing step counting.

Figure 3B:
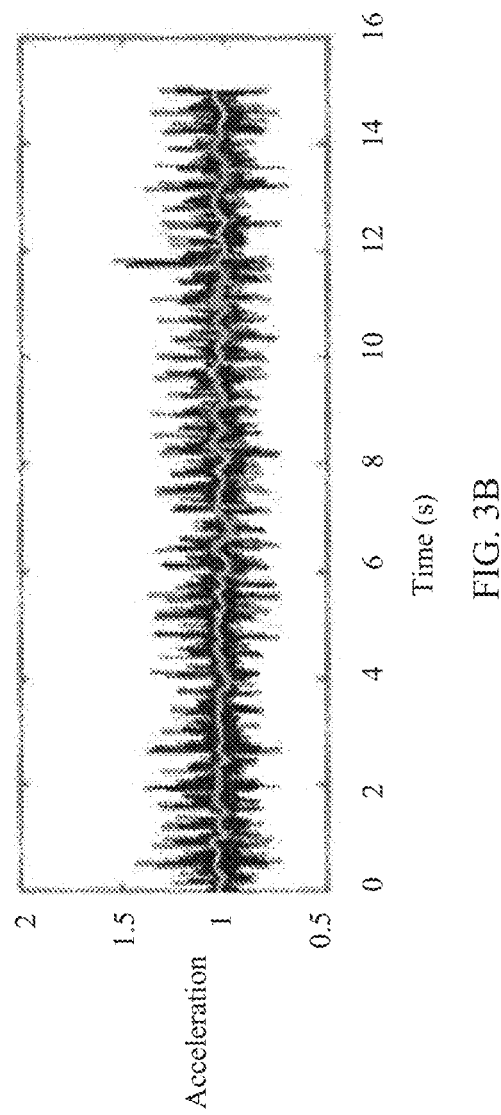

Referring to FIG. 3B, a black curve indicates the vibration signal of the user that is collected by the acceleration sensor. Fast Fourier filtering processing is performed on the vibration signal to obtain a filtered signal. For the filtered signal, refer to a white curve in FIG. 3B, In a possible implementation, before analyzing, by using the time-frequency analysis algorithm, the vibration signal to determine the quantity of exercise steps of the user on the treadmill, the terminal device may further denoise the vibration signal.

The vibration signal that is generated when the user runs and that is collected by the acceleration sensor is impacted by a vibration component of the treadmill. Therefore, the vibration component of the treadmill needs to be filtered out. Based on this, that the terminal device may denoise the vibration signal in the following manner:

identifying, by the terminal device, a vibration component of the treadmill in the vibration signal based on a vibration frequency of the treadmill; and filtering out the vibration component of the treadmill in the vibration signal, where the vibration frequency of the treadmill is a vibration frequency obtained after the treadmill is started and when no user runs on the treadmill.

Figure 3C:
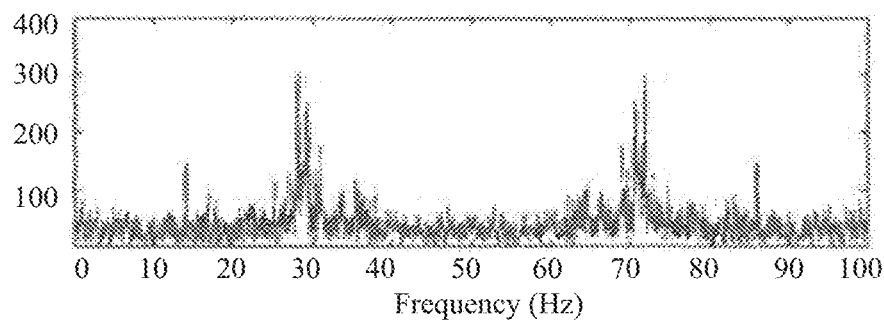
FIG. 3C is a schematic diagram of performing frequency domain conversion on a vibration signal according to an embodiment of this application.

Because the vibration component of the treadmill is very regular, a spectral component of the vibration component of the treadmill is identified, and then a corresponding spectral component in the signal collected when the user runs is filtered out, so that a relatively clean vibration signal when the user runs can be obtained, facilitating next step counting processing. Specifically, the vibration component of the treadmill in the vibration signal may be filtered out by using a finite impulse response (Finite Impulse Response, FIR for short) titter, an infinite impulse response (Infinite Impulse Response, IIR for short) filter, or the like. Referring to FIG. 3C, signals of approximately 30 Hz and 70 Hz are vibration components of the treadmill.

In a possible implementation, before collecting, by using the acceleration sensor, the vibration signal generated when the user runs on the treadmill, the terminal device identifies that the terminal device is in treadmill mode, where the treadmill mode indicates that the terminal device is placed on the treadmill. When identifying that the terminal device is in treadmill mode, the terminal device performs processing in the step counting manner for the treadmill provided in this embodiment of this application. For details, refer to the method described in FIG. 2. The terminal device may perform processing in an existing step counting manner when identifying that the terminal device is not in treadmill mode.

To implement step counting for the treadmill, the terminal device may be placed on several treadmills. Vibration components of the several treadmills are collected, and feature identification is performed on the vibration components, so that a signal feature of a treadmill is extracted by using a learning algorithm such as machine learning. In this way, when the user places the terminal device on a treadmill that is already started, a vibration component generated by the treadmill is collected, and feature identification is performed on the vibration component, to determine that the terminal device is in treadmill mode. Alternatively, when the terminal device collects, by using the acceleration sensor, a vibration signal generated when the user runs on the treadmill, the vibration signal is analyzed, to determine that the vibration signal includes a signal feature of the treadmill, thereby determining that the terminal device is in treadmill mode. To be specific, it is perceived that the user is currently running on the treadmill.

After step S202 of analyzing, by the terminal device by using a time-frequency analysis algorithm, the vibration signal to determine a quantity of exercise steps of the user on the treadmill, the terminal device may update the quantity of exercise steps of the user that is recorded in the terminal device, and notify the user of an updated quantity of exercise steps of the user. Before analyzing, by using the time-frequency analysis algorithm, the vibration signal to determine the quantity of exercise steps of the user on the treadmill, the terminal device may record a quantity of steps run by the user within a period of time, and the quantity of steps may include a quantity of exercise steps on the treadmill and a quantity of exercise steps not on the treadmill, so that the terminal device can add a currently determined quantity of exercise steps of the user on the treadmill to the recorded quantity of exercise steps. The period of time may be a day, a week, a month, or the like.

When the terminal device notifies the user of the quantity of exercise steps, the quantity of exercise steps may be displayed to the user through a display interface of a display device, or the user may be prompted with the quantity of exercise steps through voice. In addition, notifying the user in any embodiment of this application may be displaying to the user through the display interface of the display device, prompting the user through voice from a speaker, or the like. Details are not described again subsequently.

Figure 4:
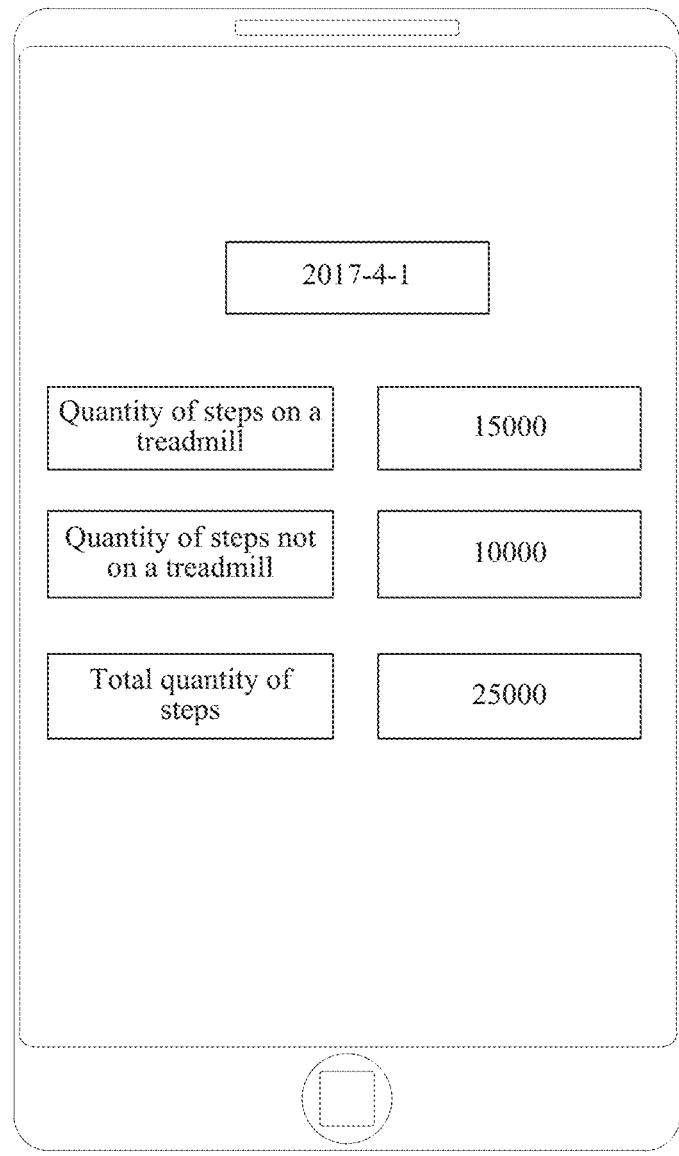
FIG. 4 is a schematic diagram of displaying a quantity of exercise steps according to an embodiment of this application.

The user can check, at any time, a quantity of running steps accumulated in the terminal device. In addition, for convenience of checking by the user, the quantity of running steps may be categorized into three types. A first type is a quantity of running steps on a treadmill, a second type is a quantity of running steps not on a treadmill, and a third type is a sum of the quantity of steps on the treadmill and the quantity of steps not on the treadmill. For example, in a day, the user starts to jog on the treadmill for an hour at eight o'clock in the morning, and a quantity of steps identified by the terminal device is 15000. A quantity of identified steps run by the user in a park in a period of time from six o'clock to half past six in the evening is 10000. Therefore, when a quantity of steps is displayed to the user, three quantities of steps may be specifically displayed on the display interface. FIG. 4 shows only a display example, and does not constitute a limit to a display manner.

In this embodiment of this application, the quantity of steps of the user on the treadmill can be calculated. In addition to this, the stride frequency of the user during running on the treadmill, and an exercise distance, speed, or the like of the user on the treadmill may further be calculated after the quantity of steps of the user on the treadmill is calculated.

The stride frequency of the user during running on the treadmill may be determined in the following manner:

recording, by the terminal device, duration of the vibration signal generated when the user runs on the treadmill; and after the terminal device analyzes, by using the time-frequency analysis algorithm, the vibration signal to determine the quantity of exercise steps of the user on the treadmill, determining, by the terminal device, based on the quantity of exercise steps of the user on the treadmill and the duration, a stride frequency of the user during running on the treadmill, and notifying the user of the stride frequency of the user.

The exercise distance of the user during running on the treadmill may be determined in the following manner:

estimating, by the terminal device, an exercise distance of the user on the treadmill based on a stride length of the user and the quantity of exercise steps of the user on the treadmill, and notifying the user of the exercise distance of the user on the treadmill, where the stride length is obtained by the terminal device by collecting statistics based on a non-treadmill running case of the user in a past period of time.

When the user does not run on the treadmill, a stride length of the user may be determined by determining a running case of the user in a past period of time by using a GPS in the terminal device.

The exercise speed of the user during running on the treadmill may be determined in the following manner:

recording, by the terminal device, duration of the vibration signal generated when the user runs on the treadmill, determining the exercise speed of the user on the treadmill based on the exercise distance determined in the foregoing manner, and notifying the user of the exercise speed.

Figure 5:
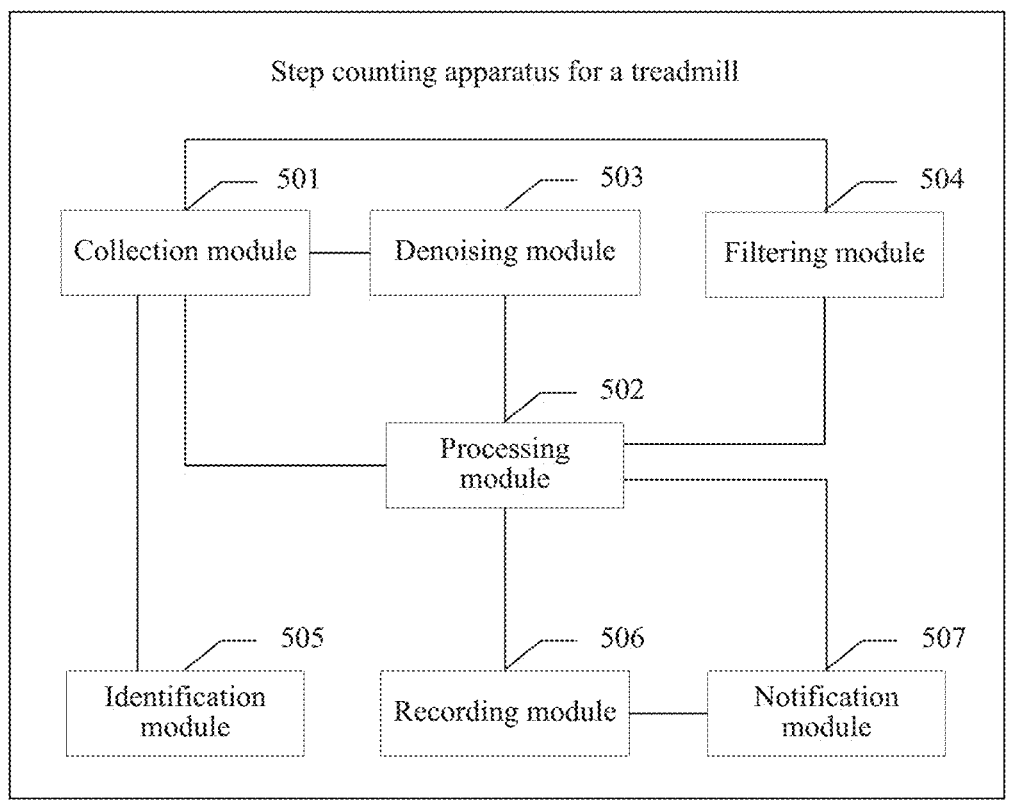
FIG. 5 is a schematic diagram of a step counting apparatus for a treadmill according to an embodiment of this application.

Based on a same inventive conception as that in the method embodiment, an embodiment of this application further provides a step counting apparatus for a treadmill. The apparatus is applied to a terminal device including an acceleration sensor. The apparatus is applied to the terminal device. The terminal device is placed on the treadmill. Specifically, the apparatus may be implemented by using the processor 120 in the mobile phone 100. As shown in FIG. 5, the apparatus may include:

a collection module 501, configured to collect, by using the acceleration sensor, a vibration signal generated when a user runs on the treadmill; and a processing module 502, configured to analyze, by using a time-frequency analysis algorithm, the vibration signal to determine a quantity of exercise steps of the user on the treadmill.

In a possible design, the apparatus further includes:

a denoising module 503, configured to denoise the vibration signal before the processing module 502 analyzes, by using the time-frequency analysis algorithm, the vibration signal to determine the quantity of exercise steps of the user on the treadmill.

In a possible design, the denoising module 503 is specifically configured to: identify a vibration component of the treadmill in the vibration signal based on a vibration frequency of the treadmill; and filter out the vibration component of the treadmill in the vibration signal, where the vibration frequency of the treadmill is a vibration frequency obtained after the treadmill is started and when no user runs on the treadmill.

In a possible design, the apparatus further includes:

a filtering module 504, configured to perform fast Fourier filtering processing on the vibration signal to obtain a filtered signal, The processing module 502 is specifically configured to determine a quantity of crests whose peaks are greater than a preset threshold in the filtered signal as the quantity of exercise steps of the user.

In a possible design, the apparatus further includes:

an identification module 505, configured to identify, before the collection module 501 collects, by using the acceleration sensor, the vibration signal generated when the user runs on the treadmill, that the terminal device is in treadmill mode, where the treadmill mode indicates that the terminal device is placed on the treadmill.

In a possible design, the apparatus further includes:

a recording module 506, configured to update, after the processing module 502 analyzes, by using the time-frequency analysis algorithm, the vibration signal to determine the quantity of exercise steps of the user on the treadmill, the quantity of exercise steps of the user that is recorded in the terminal device; and a notification module 507, configured to notify the user of an updated quantity of exercise steps of the user.

In a possible design, the recording module 506 is configured to record duration of the vibration signal generated when the user runs on the treadmill, After analyzing, by using the time-frequency analysis algorithm, the vibration signal to determine the quantity of exercise steps of the user on the treadmill, the processing module 502 determines, based on the quantity of exercise steps of the user on the treadmill and the duration, a stride frequency of the user during running on the treadmill.

The notification module 507 is configured to notify the user of the stride frequency of the user during running on the treadmill.

In a possible design, the processing module 502 is configured to: after analyzing, by using the time-frequency analysis algorithm, the vibration signal to determine the quantity of exercise steps of the user on the treadmill, estimate an exercise distance of the user on the treadmill based on a stride length of the user and the quantity of exercise steps of the user on the treadmill, where the stride length is obtained by the terminal device by collecting statistics based on a non-treadmill running case of the user in a past period of time.

The notification module 507 is configured to notify the user of the exercise distance of the user on the treadmill.

Module division in this embodiment of this application is an example, is merely logical function division, and may be other division in actual implementation. In addition, function modules in the embodiments of this application may be integrated into one processor, or each of the modules may exist alone physically, or two or more modules are integrated into one module. The integrated module may be implemented in a form of hardware, or may be implemented in a form of a functional module of software.

When the integrated module is implemented by using hardware, for hardware implementation of the terminal device, refer to FIG. 1 and related descriptions of FIG. 1.

The memory 130 is configured to store a software program.

The acceleration sensor in the sensors 170 is configured to collect a vibration signal generated when a user runs on the treadmill.

The processor 120 is configured to execute the software program stored in the memory, and is specifically configured to instruct the acceleration sensor to: collect the vibration signal generated when the user runs on the treadmill, and analyze, by using a time-frequency analysis algorithm, the vibration signal to determine a quantity of exercise steps of the user on the treadmill.

In a possible implementation, the processor 120 is further configured to denoise the vibration signal before analyzing, by using the time-frequency analysis algorithm, the vibration signal to determine the quantity of exercise steps of the user on the treadmill.

In a possible implementation, when denoising the vibration signal, the processor 120 is specifically configured to:

identify a vibration component of the treadmill in the vibration signal based on a vibration frequency of the treadmill; and filter out the vibration component of the treadmill in the vibration signal, where the vibration frequency of the treadmill is a vibration frequency obtained after the treadmill is started and when no user runs on the treadmill.

In a possible implementation, when analyzing, by using the time-frequency analysis algorithm, the vibration signal to determine the quantity of exercise steps of the user on the treadmill, the processor 120 is specifically configured to:

perform fast Fourier filtering processing on the vibration signal to obtain a filtered signal; and determine a quantity of crests whose peaks are greater than a preset threshold in the filtered signal as the quantity of exercise steps of the user.

In a possible implementation, the processor 120 is further configured to identify, before the vibration signal generated when the user runs on the treadmill is collected by using the acceleration sensor, that the terminal device is in treadmill mode, where the treadmill mode indicates that the terminal device is placed on the treadmill.

In a possible implementation, the processor 120 is further configured to:

update, after analyzing, by using the time-frequency analysis algorithm, the vibration signal to determine the quantity of exercise steps of the user on the treadmill, the quantity of exercise steps of the user that is recorded in the memory 130, and notify the user of an updated quantity of exercise steps of the user.

The user may be notified of the quantity of exercise steps through a display interface of the display device 110, or the user may be prompted through voice from the speaker 210, or the user may be prompted through a sent prompt tone.

In a possible design, the processor 120 is further configured to: record, in the memory 130, duration of the vibration signal generated when the user runs on the treadmill; and after analyzing, by using the time-frequency analysis algorithm, the vibration signal to determine the quantity of exercise steps of the user on the treadmill, determine, based on the quantity of exercise steps of the user on the treadmill and the duration, a stride frequency of the user during running on the treadmill, and notify the user of the stride frequency of the user.

The user may be notified of the stride frequency through the display interface of the display device 110, or the user may be prompted through voice from the speaker 210, or the user may be prompted through a sent prompt tone.

In a possible design, the processor 120 is further configured to: after analyzing, by using the time-frequency analysis algorithm, the vibration signal to determine the quantity of exercise steps of the user on the treadmill, estimate an exercise distance of the user on the treadmill based on a stride length of the user and the quantity of exercise steps of the user on the treadmill, and notify the user of the exercise distance of the user on the treadmill, where the stride length is obtained by the terminal device by collecting statistics based on a non-treadmill running case of the user in a past period of time.

The user may be notified of the exercise distance through the display interface of the display device 110, or the user may be prompted through voice from the speaker 210, or the user may be prompted through a sent prompt tone.

In the embodiments of this application, the acceleration sensor of the terminal device is used to collect the vibration signal of the treadmill when the user runs, and the quantity of steps of the user is identified through the time-frequency analysis algorithm. Quantities of exercise steps of the user are converged to improve social ranking performance, thereby enhancing user experience. In addition, no additional step counting device for running is needed any more, which reduces costs of the user.

A person skilled in the art should understand that the embodiments of this application may be provided as a method, a system, or a computer program product. Therefore, this application may use a form of hardware only embodiments, software only embodiments, or embodiments with a combination of software and hardware. Moreover, this application may use a form of a computer program product that is implemented on one or more computer-usable storage media (including but not limited to a disk memory, a CD-ROM, an optical memory, and the like) that include computer usable program code.

This application is described with reference to the flowcharts and/or block diagrams of the method, the device (system), and the computer program product according to the embodiments of this application. It should be understood that computer program instructions may be used to implement each process and/or each block in the flowcharts and/or the block diagrams, and a combination of a process and/or a block in the flowcharts and/or the block diagrams. These computer program instructions may be provided for a general-purpose computer, a dedicated computer, an embedded processor, or a processor of any other programmable data processing device to generate a machine, so that the instructions executed by a computer or a processor of any other programmable data processing device generate an apparatus for implementing a specific function in one or more processes in the flowcharts and/or in one or more blocks in the block diagrams.

These computer program instructions may be stored in a computer readable memory that can instruct the computer or any other programmable data processing device to work in a specific manner, so that the instructions stored in the computer readable memory generate an artifact that includes an instruction apparatus. The instruction apparatus implements a specified function in one or more processes in the flowcharts and/or in one or more blocks in the block diagrams.

These computer program instructions may also be loaded onto a computer or another programmable data processing device, so that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Obviously, a person skilled in the art can make various modifications and variations to the embodiments of this application without departing from the spirit and scope of the embodiments of this application. This application is intended to cover these modifications and variations provided that they fall within the scope of protection defined by the following claims and their equivalent technologies.

What is claimed is:

1. A step counting method for a treadmill, wherein the step counting method is implemented by an electronic device configured to be located on the treadmill, and wherein the step counting method comprises:

collecting, using an acceleration sensor, a vibration signal generated when a user runs on the treadmill; and analyzing, based on a quantity of crests having peaks greater than a preset threshold and using a time-frequency analysis algorithm, the vibration signal to determine a quantity of exercise steps of the user on the treadmill by:

performing fast Fourier filtering processing on the vibration signal to obtain a filtered signal; and determining the quantity of crests in the filtered signal having the peaks greater than the preset threshold as the quantity of exercise steps of the user.

2. The step counting method of claim 1, wherein before analyzing the vibration signal to determine the quantity of exercise steps of the user on the treadmill, the step counting method further comprises denoising the vibration signal.

3. The step counting method of claim 2, wherein denoising the vibration signal comprises:
obtaining a vibration frequency of the treadmill after the treadmill is started and while the treadmill is unused;
identifying a vibration component of the treadmill in the vibration signal based on the vibration frequency of the treadmill; and
filtering out the vibration component from the vibration signal.

4. The step counting method of claim 1, wherein before collecting the vibration signal generated when the user runs on the treadmill, the step counting method further comprises identifying that the electronic device is in a treadmill mode, and wherein the treadmill mode indicates that the electronic device is located on the treadmill.

5. The step counting method of claim 1, wherein after analyzing the vibration signal to determine the quantity of exercise steps of the user on the treadmill, the step counting method further comprises:
updating the quantity of exercise steps of the user that is recorded in the electronic device; and
notifying the user of an updated quantity of exercise steps of the user.

6. The step counting method of claim 1, further comprising:
recording a duration of the vibration signal generated when the user runs on the treadmill;
after analyzing the vibration signal to determine the quantity of exercise steps of the user on the treadmill, determining, based on the duration and the quantity of exercise steps of the user on the treadmill, a stride frequency of the user while running on the treadmill; and
notifying the user of the stride frequency of the user.

7. The step counting method of claim 1, wherein after analyzing the vibration signal to determine the quantity of exercise steps of the user on the treadmill, the step counting method further comprises:
obtaining a stride length of the user by collecting statistics when the user is running while off of the treadmill;
estimating an exercise distance of the user on the treadmill based on the stride length of the user and the quantity of exercise steps of the user on the treadmill; and
notifying the user of the exercise distance of the user on the treadmill.

8. An electronic device, comprising:
an acceleration sensor configured to collect a vibration signal generated when a user runs on a treadmill and the electronic device is placed on the treadmill;
memory configured to store a software program; and
at least one processor coupled to the acceleration sensor and the memory and configured to execute the software program stored in the memory to:
instruct the acceleration sensor to collect the vibration signal generated when the user runs on the treadmill; and
analyze, based on a quantity of crests having peaks greater than a preset threshold and using a time-frequency analysis algorithm, the vibration signal to determine a quantity of exercise steps of the user on the treadmill by:
performing fast Fourier filtering processing on the vibration signal to obtain a filtered signal; and
determining the quantity of crests in the filtered signal having the peaks greater than the preset threshold as the quantity of exercise steps of the user.

9. The electronic device of claim 8, wherein before analyzing the vibration signal to determine the quantity of exercise steps of the user on the treadmill, the processor is further configured to denoise the vibration signal.

10. The electronic device of claim 9, wherein the processor is configured to denoise the vibration signal by being configured to:
obtain, from the acceleration sensor, a vibration frequency of the treadmill after the treadmill is started and while the treadmill is unused;
identify a vibration component of the treadmill in the vibration signal based on the vibration frequency of the treadmill; and
filter out the vibration component from the vibration signal.

11. The electronic device of claim 8, wherein the processor is further configured to identify, before the vibration signal is collected using the acceleration sensor, that the electronic device is in a treadmill mode that indicates that the electronic device is located on the treadmill.

12. The electronic device of claim 8, wherein the processor is further configured to:
update, after analyzing the vibration signal to determine the quantity of exercise steps of the user on the treadmill, the quantity of exercise steps of the user that is recorded in the memory; and
notify the user of an updated quantity of exercise steps of the user.

13. The electronic device of claim 8, wherein the processor is further configured to:
record, in the memory, a duration of the vibration signal generated when the user runs on the treadmill;
after analyzing the vibration signal to determine the quantity of exercise steps of the user on the treadmill, determine, based on the quantity of exercise steps of the user on the treadmill and the duration, a stride frequency of the user while the user is running on the treadmill; and
notify the user of the stride frequency of the user.

14. The electronic device of claim 8, wherein the processor is further configured to:
obtain a stride length of the user by collecting statistics when the user is running while off of the treadmill;
after analyzing the vibration signal to determine the quantity of exercise steps of the user on the treadmill, estimate an exercise distance of the user on the treadmill based on the stride length of the user and the quantity of exercise steps of the user on the treadmill; and
notify the user of the exercise distance.

15. A non-transitory computer-readable storage medium, wherein the non- transitory computer-readable storage medium stores a software program that, when executed by one or more processors of an electronic device, causes the electronic device to:
cause an acceleration sensor to collect a vibration signal generated when a user runs on a treadmill; and
analyze, based on a quantity of crests having peaks greater than a preset threshold and using a time-frequency analysis algorithm, the vibration signal to determine a quantity of exercise steps of the user on the treadmill by:

performing fast Fourier filtering processing on the vibration signal to obtain a filtered signal; and determining the quantity of crests in the filtered signal having the peaks greater than the preset threshold as the quantity of exercise steps of the user.

16. The non-transitory computer-readable storage medium of claim 15, wherein the software program causes the electronic device to analyze the vibration signal at least in part by causing the electronic device to denoise the vibration signal.

17. The non-transitory computer-readable storage medium of claim 16, wherein the software program is configured to cause the electronic device to denoise the vibration signal at least in part by causing the electronic device to:

obtain, from the acceleration sensor, a vibration frequency of the treadmill after the treadmill is started and while the treadmill is unused;

identify a vibration component of the treadmill in the vibration signal based on the vibration frequency; and filter out the vibration component of the treadmill from the vibration signal.

18. The non-transitory computer-readable storage medium of claim 15, wherein before causing the acceleration sensor to collect the vibration signal generated when the user runs on the treadmill, the software program causes the electronic device to identify that the electronic device is in a treadmill mode, and wherein the treadmill mode indicates that the electronic device is located on the treadmill.

19. The non-transitory computer-readable storage medium of claim 15, wherein after analyzing the vibration signal to determine the quantity of exercise steps of the user on the treadmill, the software program causes the electronic device to update the quantity of exercise steps of the user that is recorded in the electronic device; and notify the user of an updated quantity of exercise steps of the user.

20. The non-transitory computer-readable storage medium of claim 15, wherein the software program further causes the electronic device to:

record a duration of the vibration signal generated when the user runs on the treadmill;

after analyzing the vibration signal to determine the quantity of exercise steps of the user on the treadmill, determine, based on the duration and the quantity of exercise steps of the user on the treadmill, a stride frequency of the user while running on the treadmill; and notify the user of the stride frequency of the user.

* * * * *